(12) United States Patent
Vivien

(10) Patent No.: US 11,911,589 B2
(45) Date of Patent: Feb. 27, 2024

(54) HOLDING DEVICE FOR INJECTION DEVICE TUBES

(71) Applicant: CROSSJECT, Dijon (FR)

(72) Inventor: Gilles Vivien, Malakoff (FR)

(73) Assignee: CROSSJECT, Dijon (FR)

( * ) Notice: Subject to any disclaimer, the term of this patent is extended or adjusted under 35 U.S.C. 154(b) by 445 days.

(21) Appl. No.: 17/227,550

(22) Filed: Apr. 12, 2021

(65) Prior Publication Data

US 2021/0236716 A1 Aug. 5, 2021

Related U.S. Application Data

(63) Continuation of application No. PCT/FR2019/052396, filed on Oct. 9, 2019.

(30) Foreign Application Priority Data

Oct. 10, 2018 (FR) ..................................... 18/59371

(51) Int. Cl.
  *B65D 25/10* (2006.01)
  *A61M 5/00* (2006.01)
  *B01L 9/06* (2006.01)

(52) U.S. Cl.
  CPC ............... *A61M 5/008* (2013.01); *B01L 9/06* (2013.01)

(58) Field of Classification Search
  CPC .................. B01L 9/06; B01L 2200/025; B01L 2300/0609; B01L 2300/0829; A61M 5/008; A61M 5/002; A61M 5/001; A61M 2207/00; B65D 25/108; B65D 1/36

USPC ........................ 206/366, 438, 364; 211/60.1
See application file for complete search history.

(56) References Cited

U.S. PATENT DOCUMENTS

| 2001/0052476 | A1 | 12/2001 | Heinz et al. | |
| 2014/0027332 | A1* | 1/2014 | Pawlowski | ........... A61M 5/008 248/346.03 |
| 2014/0034545 | A1 | 2/2014 | Pawlowski et al. | |
| 2016/0097576 | A1* | 4/2016 | Bartkowski | ............... B01L 7/50 62/340 |

FOREIGN PATENT DOCUMENTS

| DE | 102012108215 | 1/2014 |
| EP | 2119463 | 11/2009 |

(Continued)

OTHER PUBLICATIONS

International Search Report for International Application PCT/FR2019/052396, dated Jan. 30, 2020.

*Primary Examiner* — King M Chu
(74) *Attorney, Agent, or Firm* — Burris Law, PLLC

(57) ABSTRACT

A holding device intended to hold injection-device tubes of the type including an upper flange at one end of a body and a lower flange at the opposite end of the body includes orifices each intended to accept one tube, each orifice being configured to allow the tube and each of its flanges to pass. The holding device further includes a holding means configured to hold the tube through the orifice via its upper flange, the holding means having at least one elastically deformable element. The at least one elastically deformable element includes a holding end situated in line with the orifice and configured to deform as the upper flange passes through the orifice, and to support the tube via the said flange when it is inserted in the orifice.

12 Claims, 1 Drawing Sheet

(56) References Cited

FOREIGN PATENT DOCUMENTS

| | | |
|---|---|---|
| EP | 3269409 | 1/2018 |
| FR | 3038232 | 1/2017 |
| WO | 2014112113 | 7/2014 |

\* cited by examiner

HOLDING DEVICE FOR INJECTION DEVICE TUBES

CROSS-REFERENCE TO RELATED APPLICATIONS

This application is a continuation of International Application No. PCT/FR2019/052396, filed on Oct. 9, 2019, which claims priority to and the benefit of FR 18/59371, filed on Oct. 10, 2018. The disclosures of the above applications are incorporated herein by reference.

FIELD

The present disclosure relates to a device for holding tubes of a drug injection device, as well as a method for implementing such a device for holding tubes of a drug injection device.

BACKGROUND

The statements in this section merely provide background information related to the present disclosure and may not constitute prior art.

Syringes which are usually used for an injection with a needle, comprising a piston pushed by an operator, generally include a tube having a flange at an end called upper end.

In the remainder of the text, the terms "upper," "lower," "horizontal," "vertical," "top," "bottom," etc. will be used without limitation and with reference to the device in the position of use.

Another type of injection device, as disclosed by the document FR-A1-3038232, carries out needleless intradermal, subcutaneous, or intramuscular injections of active ingredients which are contained in a fluid for therapeutic use in human medicine or veterinary medicine. The fluid can be a gel or a more or less viscous liquid. These devices are single-use and contain an energy source such as a pressurized gas generator, delivering a gas which is suddenly released on a piston adjusted into a cylinder formed by a glass tube having a flange at each end, to propel the fluid contained under this piston to an injection nozzle in contact with the skin, and to inject it under this skin. The flanges generally have similar diameters.

The glass tubes for an injection device, in particular needleless injection devices, undergo, during their preparation, a complete cycle which is carried out in a controlled air environment, comprising successively a washing, a drying, a silicone deposition, a depyrogenation, and a final sterilization.

For the cycle of preparing tubes including a single flange, they are inserted into circular holding orifices formed on a tray, the single flange forming edges bearing above the orifices, and now these tubes vertically. In this manner, a set of tubes which are disposed in the same tray is easily manipulated in different apparatuses to carry out the succession of the preparation operations. The manipulation of the tubes is done easily, quickly, and securely.

This type of holding device can also be used for the cycle of preparation of tubes having flanges of different dimensions at each end, the flange of the upper end of the tube being of greater dimension than that of the lower flange.

However, for tubes, in particular made of glass, including a flange at each end having similar dimensions, it is not possible to use such a tray because the circular holding orifices having a diameter sufficient to receive the flanges of the tube, could not then retain the flange of the upper end.

To this end, it is known to have a tray comprising orifices which are provided to each receive the body of the tube, each orifice including a holding portion having dimensions smaller than the flanges so as to allow vertically blocking the flange of the upper end of the tube, the holding portion extending laterally by an insertion portion allowing the passage of the flanges.

This type of holding device allows an operator to insert the flange of the lower end of each tube into the insertion portion, then slide vertically this tube towards the holding portion. The tube is then held vertically by the upper flange thereof which is retained above the bore.

Such a tray, although satisfactory as a whole, is likely to improve, in particular with the aim of increasing the number of tubes held by a holding device, so as to increase the number of tubes which are prepared during a preparation cycle in order to increase the production capacity.

SUMMARY

This section provides a general summary of the disclosure and is not a comprehensive disclosure of its full scope or all of its features.

The present disclosure provides a holding device provided for holding tubes of an injection device of the type including an upper flange at one end of a body and a lower flange at the opposite end of the body. The holding device comprises orifices provided to each receive a tube, wherein each orifice is configured to pass the tube and each of the flanges thereof, and wherein the holding device includes holding means configured to hold the tube through the orifice by the upper flange thereof. The holding means has at least one elastically deformable element, said elastically deformable element including a holding end located perpendicular to the orifice and configured to be deformed during the passage of the upper flange through the orifice, and to support the tube by said flange when it is inserted into the orifice.

The holding device is for example a tray.

The term "tray" will mean any holding device.

The holding device comprises a plurality of holding means, each holding means being configured to hold one of the tubes through one of the orifices by the upper flange thereof.

Additionally, the holding device comprises an orifice retaining means. In other words, each holding means is associated with an orifice.

The elastically deformable element is elastically deformable such that it is configured to be mechanically stressed by the upper flange and to be deformed on the passage thereof.

The holding end is configured to support the tube by the upper flange thereof when the mechanical stress is removed.

Furthermore, the holding end defines a holding surface.

The term "located perpendicular to the orifice" means that the holding end is located in the orifice or on the path of the tube when it is inserted into the orifice.

The holding means is configured to hold a tube in the support position through the orifice.

More particularly, the holding means is configured to hold the tube vertically, the upper flange of the tube resting on the holding end.

As such, in a simple, fast, and efficient manner, an operator can insert each tube into an orifice, the tube then being held vertically by the upper flange thereof.

Furthermore, the orifices of this tray are such that they allow a space-saving on the tray, so as to allow storing additional tubes.

The tray according to the present disclosure may further include one or more of the following features, which can be combined with each other.

For example, the holding device comprises a plate, and the plate may be flat. The orifices are then formed in the plate.

In particular, the holding means is configured to be at least partially in contact with the body of the tube when the tube is inserted into the orifice, which allows an additional holding of the tube.

According to one form, the holding means is secured to the tray. More specifically, each of the holding means is secured to the plate.

The holding means and the tray are formed in one piece. More specifically, each of the holding means and the plate are formed integrally.

In one form of the present disclosure, the holding means protrudes upwards.

For example, each of the holding means protrudes from the plate.

According to another form, the holding means forms a wall for the orifice, the wall being protruding from the tray. More specifically, the wall protrudes from the plate.

According to yet another form, each holding means forms a wall encircling one of the orifices.

The term "wall" means a protruding element which encircles the orifice, said element being able to be openwork by including spaces.

The wall can be openwork.

This wall increases holding the tubes in the tray. In other words, the wall allows improving holding the tubes in the tray.

According to one form, the wall has a proximal end in contact with the tray and, more specifically, in contact with the plate, and a distal end forming the holding end located perpendicular to the orifice, said holding end forming an opening configured to be deformed during the passage of the upper flange of the tube through the orifice and to support the tube by said flange when it is inserted into the orifice.

The opening is of a dimension smaller than the orifice and configured to be of a dimension smaller than the upper flange of the tube.

The wall is elastically deformable such that it is configured to deviate during the passage of the upper flange.

The elastically deformable element has at least two legs. In one form, the elastically deformable element has between three and ten legs and, in another form, the elastically deformable element has six legs.

The legs of the elastically deformable element form the wall.

In this manner, the wall has spaces which are disposed between the legs, which allow said wall to deviate during the passage of the upper flange through the orifice.

According to one feature, the orifice is configured to be complementary to the upper flange.

The term "complementary" means that the shape of the orifice is substantially identical to that of the upper flange, but the dimensions thereof are slightly greater to allow the passage of said flange when the tube is inserted into the orifice. In other words, the orifice and the upper flange of the tube are configured to cooperate in a form-fitting manner.

In this manner, no space is wasted on the tray, which allows for improved production capacities.

In one form, the tray includes a plastic material comprising liquid crystal polymers, implemented by injection. This plastic material has a good rigidity, a resistance to different chemical agents, and a resistance to high temperatures of dry sterilization.

It should be noted that the previously described tray is configured to hold tubes of the type including a single flange at an upper end of a body, and/or tubes of the type including an upper flange and a lower flange, the upper flange being of a dimension which is greater than or equal to the lower flange.

In some forms, the diameter of the orifice is comprised between 15 and 20 mm and may be, for example, 16 mm.

In some forms, the diameter of the opening is comprised between 10 and 15 mm and may be, for example, 12 mm.

The present disclosure further relates to an assembly comprising:
- a holding device in accordance with any one of aforementioned features, and
- tubes for an injection device including an upper flange at one end of a body and a lower flange at the opposite end of the body, each tube being configured to be inserted into an orifice of the holding device.

The present disclosure also relates to a method for implementing a tray as previously described, for holding tubes of a drug injection device, in which a tube is inserted vertically into each orifice of the tray.

In the form according to which the holding means is protruded upwards, the method for implementing the tray comprises a step of inserting a tube into each orifice from the bottom of the tray.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
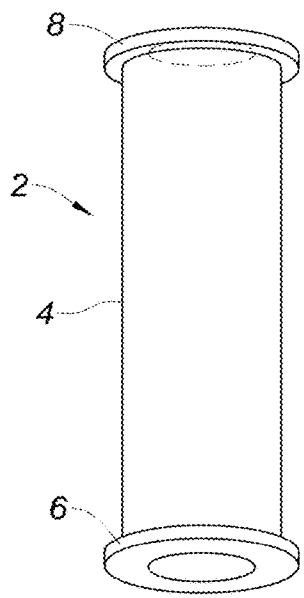
FIG. 1 is a schematic perspective side view of a tube of a needleless injection device of the type including a flange at each end of a body according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The terms "upper," "lower," "front," "rear," "top," "bottom," and the derivatives thereof refer to the position or the orientation of an element or a component, this position or this orientation being considered when the tray is in the use configuration.

FIG. 1 represents an injection device glass tube 2, including a cylindrical body 4 having a lower flange 6 at one end of the body 4 and an upper flange 8 at the opposite end of the cylindrical body 4, each forming an outer bead of revolution about a main axis of the body.

The upper flange 8 and lower flange 6 are circular.

The glass tube 2 can be used in particular by the injection device presented above and illustrated by FR-A1-3038232.

Figure 2:
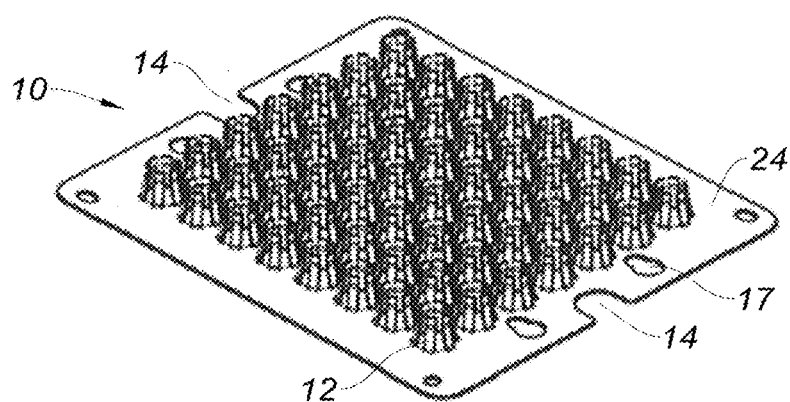
FIG. 2 is a schematic perspective top view of a tray with orifices according to the present disclosure, provided to receive tubes of FIG. 1.

FIG. 2 illustrates a tray 10 of a rectangular shape.

In one form, the tray 10 is made by injection molding of a plastic material comprising liquid crystal polymers, called "LCP," which are materials with high mechanical performance resistant to the dry heat cycle at 240° C., as well as to different chemical agents.

The tray 10 includes a flat plate 24 comprising, in the middle of two opposite sides, a notch 14 facilitating the manipulation of this tray.

The tray 10 includes eight identical rows, parallel to the sides including the notches 14, of seven circular orifices 12.

Figure 5:
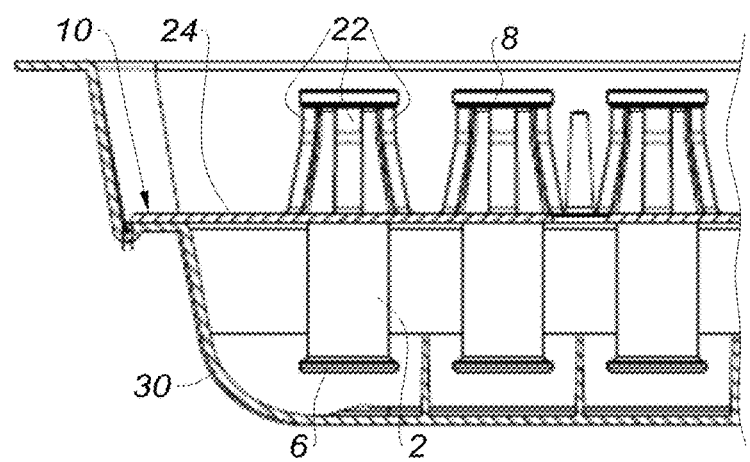
FIG. 5 is a schematic side view of a detail of the tray of FIG. 2, with the tubes being inserted into the orifices.

Each orifice 12 is provided to receive a glass tube 2 which is held vertically, by having the axis thereof perpendicular to this tray (FIG. 5).

Figure 3:
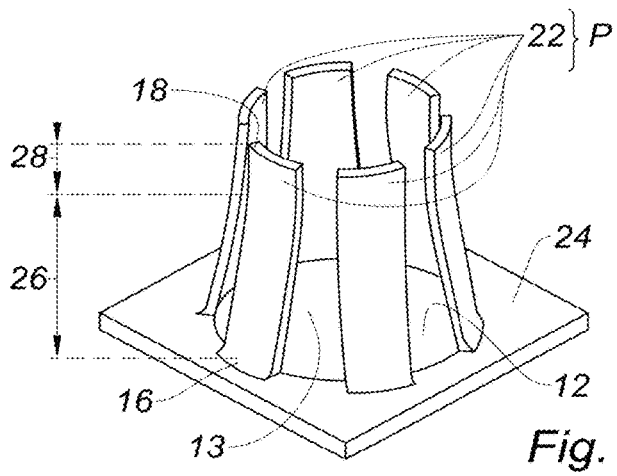
FIG. 3 is a schematic perspective view of an orifice of the tray of FIG. 2.

As illustrated in more detail in FIG. 3, each orifice 12 includes six legs 22 protruding upwardly from the tray, forming a wall P for the orifice, openwork by spaces 13 between the legs 22.

In one form, the six legs 22 are oriented at 30°.

In variants which are not shown, the orifice includes three legs or four legs.

The presence of the six legs allows for better holding of the tubes

This openwork wall P is configured to hold a tube 2 through the orifice 12, by the upper flange 8 thereof, as will be described in more detail with regard to FIG. 5.

The wall P is means for holding a tube.

Each leg 22 has a proximal end 16 in contact with the plate 24 of the tray 10 at the contour of the orifice 12, and a distal end called holding end 18, located perpendicular to the orifice 12.

Thus, each leg 22 is secured to the tray 10 and the holding end 18 is located on the path of the tube 2 when it is inserted through the orifice.

Each leg 22 is elastically deformable such that it is adapted to be deformed during the passage of the upper flange 8 from the proximal end 16 to the holding end 18, and to support the upper flange 8 when the tube 2 is inserted through the orifice 12, as illustrated in FIG. 5.

Thus, each leg is configured to be mechanically stressed by the upper flange 8 and to be deformed on the passage thereof.

The holding end 18 is configured to support the tube 2 by the upper flange 8 thereof when the mechanical stress is removed.

The holding ends 18 of each leg 22 of an orifice 12 define a holding surface located perpendicular to the orifice.

The holding surface forms an opening 20 (FIG. 4) located perpendicular to the orifice 12, configured to be deformed during the passage of the upper flange 8 and to support the tube 2 by the upper flange 8 thereof when it is inserted through the orifice 12, as represented in FIG. 5.

Moreover, each leg 22 has an obliquely upward proximal portion 26, starting from the proximal end 16 towards the inside of the orifice 12, and a vertically upward distal portion 28, starting from the proximal portion 26 towards the holding end 18.

Furthermore, the height of each leg 22 is comprised between 10 and 25 mm, in one form 18.5 mm, in order to provide for vertically holding the tubes 2 inserted into the orifices 12.

The height of the proximal portion 26 is comprised between 10 and 15 mm, in one form 13 mm, while the height of the distal portion 28 is comprised between 3 mm and 5 mm, in one form 4 mm.

Figure 4:
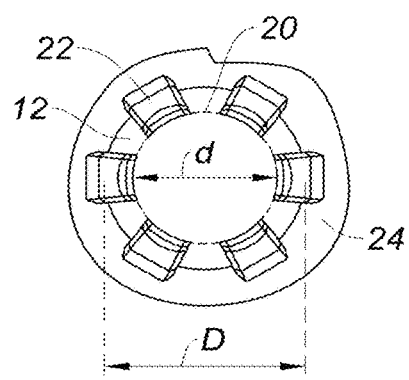
FIG. 4 is a schematic top view of the orifice of FIG. 3.

As shown in FIG. 4, the diameter "d" of the opening 20 is 12.2 mm, while the diameter "D" of the orifice 12 is 16 mm.

Thus, the opening 20 is of a dimension smaller than the orifice 12.

Furthermore, the upper flange 8 has a diameter in the range of 14 mm. It is therefore of dimension complementary to the orifice 12 but of dimension greater than the opening 20.

FIG. 5 illustrates a portion of the tray 10 including tubes 2 which are inserted into orifices 12 as previously described, the tray 10 being adjusted into a standardized support 30 forming a contour, also called "Tub," allowing a positioning in different apparatuses for processing glass tubes 2.

The tray 10 includes lumens 17 in the form of a "keyhole" which are used to grip the tray during its extraction from the standardized support 30.

Each orifice 12 is configured to pass a tube 2 and each of the flanges 6, 8 thereof.

The wall P of an orifice 12, formed by the legs 22, is configured to hold the tube 2 in the support position through the orifice 12.

Thus, each tube 2 is held vertically, the upper flange 8 resting on the holding end 18 of the legs 22.

The legs 22 are configured to be at least partially in contact with the body 4 of the tube 2 which is inserted into the orifice 12, which allows an additional holding of the tube.

It is the distal portion 28 of the legs 22 which is in contact with the body 4 of the tube 2 when it is inserted into an orifice 12.

The distal portion 28 is substantially adjusted around the body 4 of a glass tube 2.

For the insertion of a tube 2 into an orifice 12, the tube 2 is inserted vertically into the orifice 12, from the bottom of the tray 10.

When the tubes 2 have been inserted into the orifices 12 of the tray 10, the complete tray 10 is then bagged with the standardized support 30 thereof, and this bag is sealed to carry out a sterilization of the tubes.

Bags made of plastic material are made using a high density polyethylene, which can in particular be a material marketed under the registered trademark Tyvek™, allowing a reduced passage of humidity, a good heat conduction, a strong microbial barrier, and a high mechanical resistance, in particular for the resistance to perforations.

The final packaging is carried out according to the French standard NF ISO 11040-7, specifying the package of systems for delivering sterilized tubes ready to be filled.

After washing the tubes 2, a silicone coating is carried out, followed by a sterilization by a pyrogen reduction method comprising a dry-heat heating in order to obtain a strong reduction of endotoxins which are pyrogens.

In particular, a dry-heat heating cycle at 240° C. allows for simultaneously carrying out a crosslinking of the silicone, which subsequently inhibits release of this silicone into the drug after filling the glass tube 2, and during the end use of the injection device on the patient. In addition, this method avoids a sterilization with ethylene oxide which introduces toxic materials.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A holding device for holding tubes of an injection device, each of the tubes including a body, an upper flange at one end of the body, and a lower flange at an opposite end of the body, the holding device comprising:
   a tray that defines orifices, each of the orifices being configured to receive a tube of the tubes, each of the orifices being configured to allow passage of the tube including each of the upper flange and the lower flange thereof; and
   holders, each of the holders being configured to hold one of the tubes through a corresponding one of the orifices by the upper flange thereof, each of the holders having an elastically deformable element, said elastically deformable element including a proximal end and a holding end, wherein the proximal end is located proximal the tray, wherein the holding end is distal to the tray and located in line with the corresponding one of the orifices, the holding end being configured to be deformed during the passage of the upper flange through the corresponding one of the orifices, and wherein the holding end is configured to support the tube by said upper flange when the tube is inserted into the corresponding one of the orifices and said holding end is configured to be in contact with the body of the tube when the tube has been inserted into the corresponding one of the orifices, and wherein each elastically deformable element has an obliquely upward proximal portion, extending from the proximal end towards an inside of the corresponding one of the orifices, and a vertically upward distal portion, extending from the obliquely upward proximal portion towards the holding end.

2. The holding device according to claim 1, wherein the holders protrude upwards.

3. The holding device according to claim 1, wherein each of the holders forms a wall for the corresponding one of the orifices, the walls protruding from the tray of the holding device.

4. The holding device according to claim 3, wherein said holding end forms an opening configured to be deformed during the passage of the upper flange of the tube through the corresponding one of the orifices.

5. The holding device according to claim 4, wherein a diameter of the opening is between 10 and 15 mm.

6. The holding device according to claim 1, wherein the elastically deformable element has at least two legs.

7. The holding device according to claim 6, wherein the at least two legs form a wall.

8. The holding device according to claim 1, wherein each of the orifices is configured to be complementary to the upper flange.

9. The holding device according to claim 1, wherein a diameter of each of the orifices is between 15 and 20 mm.

10. An assembly comprising:
    the holding device according to claim 1; and
    the tubes, each of the tubes being inserted into the corresponding one of the orifices of the holding device.

11. A method for implementing the holding device according to claim 1, the method comprising:
    inserting the tubes vertically into each corresponding one of the orifices of the holding device.

12. The method for implementing a holding device according to claim 11, wherein each of the tubes is inserted vertically into each corresponding one of the orifices from a bottom of the holding device.

\* \* \* \* \*